(12) United States Patent
Headley et al.

(10) Patent No.: US 6,632,191 B1
(45) Date of Patent: Oct. 14, 2003

(54) SYSTEM AND METHOD FOR SEPARATING BLOOD COMPONENTS

(75) Inventors: Thomas D. Headley, Wellesley, MA (US); Edward T. Powers, Hampton Falls, NH (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 09/271,594

(22) Filed: Mar. 17, 1999

Related U.S. Application Data

(63) Continuation-in-part of application No. 08/843,218, filed on Apr. 14, 1997, now Pat. No. 6,099,491, which is a continuation of application No. 08/322,601, filed on Oct. 13, 1994, now Pat. No. 5,733,253, which is a continuation-in-part of application No. 08/835,680, filed on Apr. 9, 1997, now Pat. No. 6,007,509, which is a continuation of application No. 08/482,617, filed on Jun. 7, 1995, now Pat. No. 5,651,766.

(51) Int. Cl.⁷ ............... A61M 37/00; C02F 1/38; B04B 13/00; B04B 7/16; B04B 7/02
(52) U.S. Cl. ............ 604/6.01; 604/6.02; 604/6.03; 604/6.04; 604/6.09; 604/6.1; 604/6.15; 210/782; 494/11; 494/36; 494/37; 494/41; 494/45; 494/56; 494/60; 494/64
(58) Field of Search ............... 604/4, 4.01, 5.01, 604/6.01–6.07, 6.1, 6.11, 6.15, 6.16; 210/767, 782, 781, 784, 739, 741; 494/10, 28, 36–38, 40, 43, 45, 41, 56, 57, 11, 60, 61, 64

(56) References Cited

U.S. PATENT DOCUMENTS

| | | | |
|---|---|---|---|
| 2,661,150 A | 12/1953 | Abbott, Jr. | |
| 3,096,283 A | 7/1963 | Hein | |
| 3,239,136 A | 3/1966 | Hein | |
| 3,244,362 A | 4/1966 | Hein | |
| 3,244,363 A | 4/1966 | Hein | |
| 3,456,875 A | 7/1969 | Hein | |
| 3,737,096 A | 6/1973 | Jones et al. | |
| 4,007,871 A | 2/1977 | Jones et al. | |
| 4,010,894 A | 3/1977 | Kellogg et al. | |
| 4,056,224 A | 11/1977 | Lolachi | |
| 4,082,217 A | 4/1978 | Westberg | |
| 4,086,924 A | 5/1978 | Latham, Jr. | |

(List continued on next page.)

FOREIGN PATENT DOCUMENTS

| | | |
|---|---|---|
| EP | 0 578 086 A1 | 1/1994 |
| FR | 2 258 898 | 1/1975 |
| GB | 2 047 110 A | 11/1980 |
| WO | WO 85/02561 | 6/1985 |
| WO | WO 96/11747 | 4/1996 |

*Primary Examiner*—Angela Sykes
*Assistant Examiner*—Patricia Bianco
(74) *Attorney, Agent, or Firm*—Bromberg & Sunstein LLP

(57) ABSTRACT

A system for collecting red blood cells (RBCs) and other blood components that reduces the need for human intervention. A disposable set is provided having a port, an RBC container, a centrifuge rotor having a variable total volume, and a filter, along with tubing connecting the port, the container, the rotor and the filter. A control unit is also provided and includes a spinner in which the rotor may be held, a flow-control arrangement for controlling flow among the various components of the disposable set, and an electronic controller. The whole blood is directed by the flow-control arrangement from the port through the tubing to the rotor. The rotor includes an elastic diaphragm, and the control unit's flow-control arrangement includes a pump or other device for applying a positive and negative pressure to the rotor's elastic diaphragm. The spinner rotates the rotor so as to separate the whole blood into plasma and RBCs. Preferably, the plasma, is urged out of the rotor first, while the rotor is still being spun. After the plasma has been removed from the rotor, the RBCs are urged from the rotor through the filter, so that white blood cells (WBCs) are caught in the filter and RBCs pass through the filter to an RBC container.

28 Claims, 6 Drawing Sheets

U.S. PATENT DOCUMENTS

| | | | |
|---|---|---|---|
| 4,142,670 A | 3/1979 | Ishimaru et al. | |
| 4,151,844 A | 5/1979 | Cullis et al. | |
| 4,285,464 A | 8/1981 | Latham, Jr. | |
| 4,300,717 A | 11/1981 | Latham, Jr. | |
| 4,303,193 A | 12/1981 | Latham, Jr. | |
| 4,321,921 A | 3/1982 | Laszczower | |
| 4,387,848 A | 6/1983 | Kellogg et al. | |
| 4,430,072 A | 2/1984 | Kellogg et al. | |
| 4,447,221 A | 5/1984 | Mulzet | |
| 4,457,747 A | 7/1984 | Tu | |
| 4,482,342 A | 11/1984 | Lueptow et al. | |
| 4,512,763 A * | 4/1985 | Schneider | 604/5 |
| 4,530,691 A * | 7/1985 | Brown | 494/45 |
| 4,643,714 A | 2/1987 | Brose | |
| 4,647,279 A | 3/1987 | Mulzet et al. | |
| 4,680,025 A * | 7/1987 | Kruger et al. | 604/6 |
| 4,708,712 A | 11/1987 | Mulzet | |
| 4,734,089 A | 3/1988 | Cullis | |
| 4,806,252 A | 2/1989 | Brown et al. | |
| 4,850,995 A | 7/1989 | Tie et al. | |
| 4,889,524 A | 12/1989 | Fell et al. | |
| 4,911,833 A | 3/1990 | Schoendorfer et al. | |
| 4,934,995 A | 6/1990 | Cullis | |
| 4,936,998 A * | 6/1990 | Nishimura et al. | 210/638 |
| 4,940,543 A | 7/1990 | Brown et al. | |
| 4,968,295 A | 11/1990 | Neumann | |
| 4,983,158 A | 1/1991 | Headley | |
| 4,985,153 A | 1/1991 | Kuroda et al. | |
| 5,039,401 A | 8/1991 | Columbus et al. | |
| 5,045,048 A * | 9/1991 | Kaleskas et al. | 494/41 |
| 5,112,298 A | 5/1992 | Prince et al. | |
| 5,114,396 A | 5/1992 | Unger et al. | |
| 5,141,486 A | 8/1992 | Antwiler | |
| 5,154,716 A | 10/1992 | Bauman et al. | |
| 5,174,894 A | 12/1992 | Ohsawa et al. | |
| 5,217,426 A | 6/1993 | Bacehowski et al. | |
| 5,217,427 A | 6/1993 | Cullis | |
| 5,234,403 A | 8/1993 | Yoda et al. | |
| 5,273,517 A | 12/1993 | Barone et al. | |
| 5,277,701 A | 1/1994 | Christie et al. | |
| 5,298,016 A | 3/1994 | Gordon | |
| 5,300,060 A | 4/1994 | Nelson | |
| 5,316,540 A | 5/1994 | McMannis et al. | |
| 5,318,512 A | 6/1994 | Neumann | |
| 5,368,542 A | 11/1994 | McMannis et al. | |
| 5,386,734 A | 2/1995 | Pusinelli | |
| 5,387,174 A | 2/1995 | Rochat | |
| 5,387,187 A * | 2/1995 | Fell et al. | 604/6.02 |
| 5,417,650 A | 5/1995 | Gordon | |
| 5,437,598 A | 8/1995 | Antwiler | |
| 5,470,483 A | 11/1995 | Bene et al. | |
| 5,484,396 A | 1/1996 | Naficy | |
| 5,543,062 A | 8/1996 | Nishimura | |
| 5,637,082 A * | 6/1997 | Pages et al. | 604/6.11 |
| 5,651,766 A | 7/1997 | Kingsley et al. | |
| 5,728,060 A | 3/1998 | Kingsley et al. | |
| 5,733,253 A | 3/1998 | Headley et al. | |
| 5,779,660 A | 7/1998 | Kingsley et al. | |
| 5,904,355 A * | 5/1999 | Powers | 277/389 |
| 5,954,971 A | 9/1999 | Pages et al. | 210/739 |
| 6,207,063 B1 * | 3/2001 | Brown | 210/739 |
| 6,221,315 B1 * | 4/2001 | Giesler et al. | 422/101 |

* cited by examiner

SYSTEM AND METHOD FOR SEPARATING BLOOD COMPONENTS

RELATED APPLICATIONS

The present application is a continuation-in-part of U.S. patent application Ser. No. 08/843,218, filed Apr. 14, 1997, which application has now issued as U.S. Pat. No. 6,099, 491; which is a continuation of U.S. patent application Ser. No. 08/322,601, filed Oct. 13, 1994 for an invention of Headley and Powers, which application has now issued as U.S. Pat. No. 5,733,253. The present application is also a continuation-in-part of U.S. patent application Ser. No. 08/835,680, filed Apr. 9, 1997, which application has now issued as U.S. Pat. No. 6,007,509; which in turn is a continuation of U.S. patent application Ser. No. 08/482,617, filed Jun. 7, 1995 for an invention of Kingsley, Headley and Halpern, which application has now issued as U.S. Pat. No. 5,651,766. All these applications are incorporated herein by reference.

TECHNICAL FIELD

This invention generally relates to systems and methods for processing blood and other biological fluids.

BACKGROUND ART

FIG. 1 shows a typical disposable bag set used in the prior art to process blood. The set includes a needle 10 or cannula, which is inserted into a vein of a donor. The needle 10 is connected to the tube 11, which in turn is connected to collection bag 12, so as to allow whole blood to flow from the donor through the needle 10 and the tube 11 into collection bag 12. The collection bag 12 contains anticoagulant. After the desired amount of blood has been collected into collection bag 12, the needle 10 is removed from the donor, and tube 11 is cut and heat sealed. The remainder of the bag set is then brought to a centrifuge, which spins the bag set so that the blood in collection bag 12 separates into plasma and red blood cells. Typically, the centrifuge is not located at the point where the blood donation takes place.

After the blood has separated into plasma and red blood cells (RBCs), the bag set is removed from the centrifuge. The plasma component is urged from collection bag 12 through tube 13 into plasma-storage bag 14. The tube leading to the plasma-storage bag 14 is then cut and heat sealed. Storage-solution bag 16 holds RBC-storage solution. After the plasma component has been urged into the plasma-storage bag 14, the RBC-storage solution is urged from the storage-solution bag 16 into the collection bag 12. Tube 13 is then cut and heat sealed.

The remaining portion of the bag set consists of the collection bag 12, which now holds primarily RBCs (along with storage solution), filter 17, RBC-storage bag 18, and the tubing that connects these components. The collection bag 12 is then hung, so that gravity causes the RBC component to pass through the filter 17 to RBC-storage bag 18. The filter 17 removes white blood cells (WBCs) from the RBCs. After the RBCs (and storage solution) pass into the RBC-storage bag 18, tube 19 is cut and heat sealed.

This prior-art process of collecting and separating blood components involves many steps and frequent human intervention. The arrangement of the prior-art bag set does not permit the process to be easily automated.

SUMMARY OF THE INVENTION

The present invention is directed to systems and methods for collecting blood components, and in particular, systems and methods that reduce the need for human intervention.

In a preferred embodiment, a disposable set is provided having a port, an RBC container, a centrifuge rotor having a variable total volume, and a filter, along with tubing connecting the port, the container, the rotor and the filter. A control unit is also provided. The control unit preferably includes a spinner in which the rotor may be held, a flow-control arrangement for controlling flow among the various components of the disposable set, and an electronic controller.

The controller may be used to control the spinner and the flow-control arrangement.

Preferably, the rotor is placed in the spinner, before whole blood is drawn through the port. The port is preferably a needle or other cannula inserted into a vein of the donor. The whole blood is directed by the flow-control arrangement from the port through the tubing to the rotor. In a preferred embodiment, the rotor includes a flexible diaphragm, and the control unit's flow-control arrangement includes a pump or other device for applying a negative pressure to the rotor's flexible diaphragm, so as to draw fluid into the rotor. The rotor is also preferably provided with a fixed portion, a rotatable portion and a rotary seal providing a seal between the fixed and rotatable portions, and the tubing may be connected to the rotor's fixed portion.

The spinner rotates the rotor so as to separate the whole blood into a first component and a second component, wherein the first component is primarily plasma, and wherein the second component is primarily red blood cells (RBCs) and includes white blood cells (WBCs). Preferably, the first component, the plasma, is urged out of the rotor first, while the rotor is still being spun to keep the first and second components separated. In one preferred embodiment, the needle is removed from the donor before any of the components are urged from the rotor. The plasma is preferably directed to and stored in a plasma-storage container. After the plasma has been removed from the rotor, the second component, containing red blood cells and white blood cells is urged from the rotor through the filter, so that white blood cells are caught in the filter and red blood cells pass through the filter. After passing through the filter, the red blood cells are stored in an RBC container.

In alternative preferred embodiments, a cannula remains in the donor so as to return the plasma component to the donor. Two separate cannulas may be used for drawing whole and returning the plasma component. In a preferred embodiment, a single cannula is used to draw whole blood and to return the plasma component; in this embodiment, a temporary storage container is used to hold the plasma while whole blood is being collected, and the plasma is returned when the red blood cells are being processed by and urged from the rotor.

DESCRIPTION OF SPECIFIC EMBODIMENTS

Figure 1:
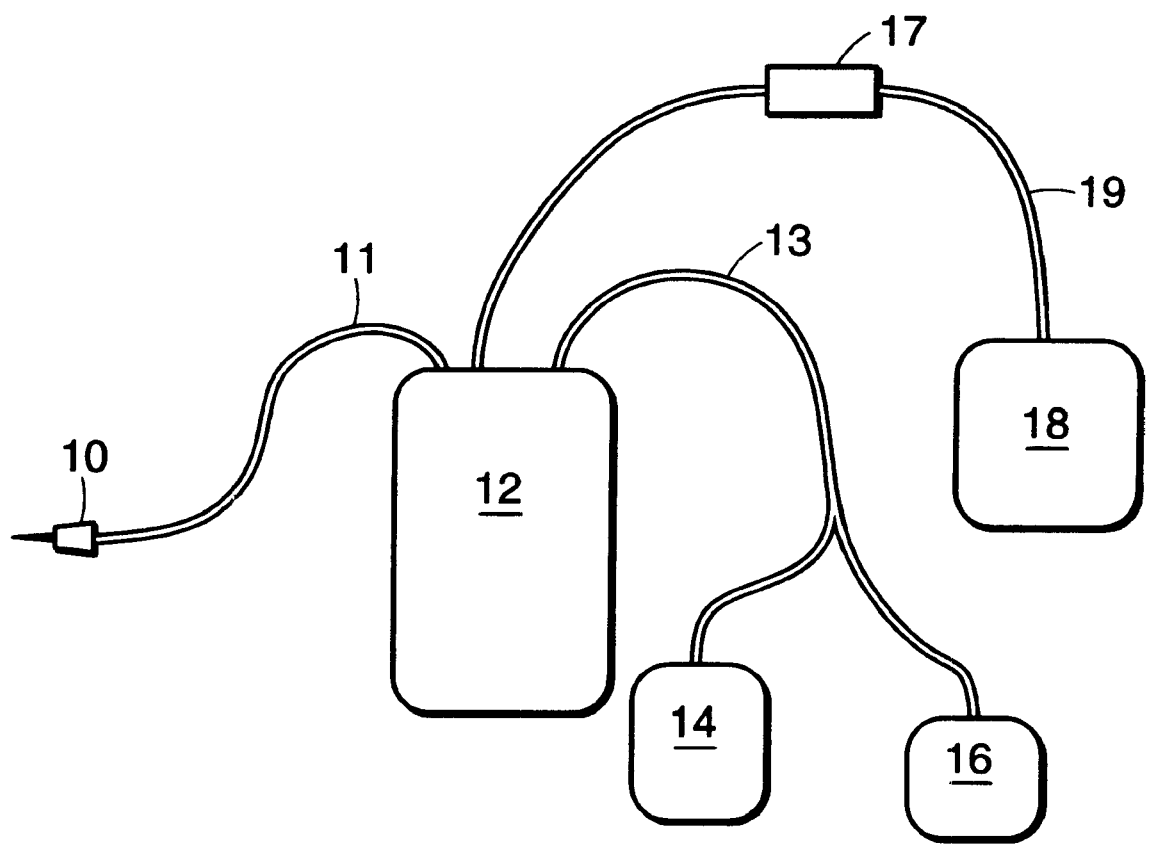
FIG. 1 shows a disposable set that may be used in a prior-art system for processing blood.
Figure 2:
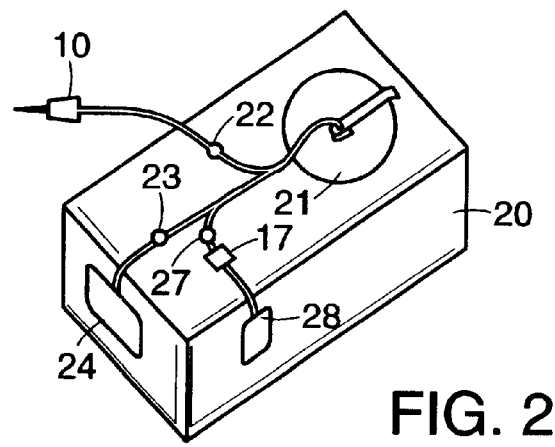
FIG. 2 shows a system according to the present invention.

FIG. 2 shows an embodiment of a system according to the present invention. The system uses many of the components and features described in above-referenced U.S. Pat. Nos. 5,733,253 and 5,651,766, which have been incorporated herein by reference.

Figure 3:
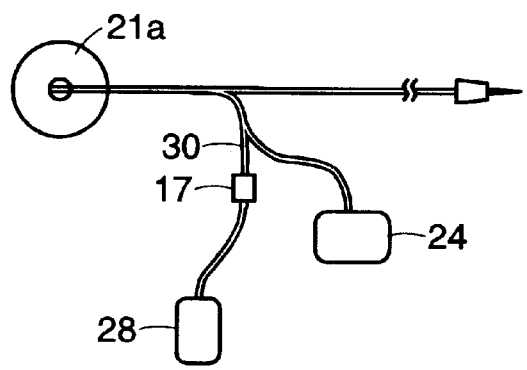
FIG. 3 shows a disposable set that may be used in the system shown in FIG. 2.

The system includes a disposable set, depicted in FIG. 3, and a control unit 20 into which the disposable set is mounted. The disposable set includes an access means for withdrawing blood, such as a cannula 10, a needle, or alternatively a connector for attachment to a shunt or other arrangement for permitting whole blood to enter the disposable set. Before whole blood is drawn from the donor, the disposable set is mounted in the control unit, and of course the cannula 10 is connected to the donor. The whole blood passes through tubing connecting the various components of the disposable set and flows into the centrifuge rotor 21 mounted in the control unit 20. The rotor 21 preferably has a variable total volume and, in a preferred embodiment, is of the type described in above-referenced U.S. Pat. Nos. 5,733,253 and 5,651,766. Blood may be drawn into the rotor 21 by creating a vacuum in the chuck that holds the rotor 21. Alternatively, a peristaltic pump or other flow-inducing arrangement may be used, in lieu of or in addition to valve 22, to draw the whole blood from the cannula 10 into the rotor 21.

The rotor 21 is held by a spinner means for loading and spinning the rotor, such as a chuck in the control unit 20. The chuck spins the rotor 21 in order to separate the blood into its components. The preferred embodiment of the rotor 21 has an elastic diaphragm that defines the interior volume of the rotor 21. As discussed in the above-referenced U.S. Pat. Nos. 5,733,253 and 5,651,766, the elastic diaphragm permits the total volume of the rotor 21 to be varied by varying the air pressure applied through the chuck to the elastic diaphragm; this air pressure is also preferably controlled by the control unit. This air pressure may also be used to force fluid from the rotor 21 by increasing the air pressure sufficiently or to draw fluid into the rotor 21 by decreasing air pressure sufficiently.

As whole blood is introduced to the rotor, it is preferable that anticoagulant be added to the whole blood. The anticoagulant may be provided from an anticoagulant/plasma-storage container 24 (preferably a bag). As the flow of blood from cannula 10 is regulated by valve 22, which is controlled by control unit 20, the anticoagulant is metered into the blood in the appropriate proportion by valve 23, which is also controlled by the control unit. In lieu of or in addition to valve 23, a peristaltic pump or other flow-inducing arrangement may be used to add the anticoagulant to the whole blood. After the blood has been separated into components, the plasma component may be stored in the same container 24 from which anticoagulant was removed. In an alternative embodiment, separate containers may be used for holding the anticoagulant and storing the separated plasma component. In a preferred embodiment, the tubing may be modified so that the anticoagulant is added to the whole blood coming from the donor at a point in the tubing much closer to the cannula 10.

When a sufficient amount of whole blood has entered the rotor 21, the rotor is spun sufficiently fast so as to separate the blood into plasma and red blood cell components. After separation, one of the components is removed from the rotor 21. Preferably, the plasma is urged from the rotor first and is then directed through the valve 23 to the anticoagulant/plasma-storage container 24. In the embodiment depicted in FIG. 2, the donor is preferably disconnected from the system before any plasma is urged from the rotor 21. In a further preferred embodiment, the donor is disconnected from the system before the rotor is spun to separate the blood into plasma and red blood cell components This method and system may be modified so that platelets are separately collected in the manner set forth in concurrently filed application Ser. No. 09/271,601, for a "System and Method for Collecting Platelets and Other Blood Components," and listing Thomas D. Headley as an inventor.

This concurrently filed application is incorporated herein by reference.) When substantially all of the plasma has been removed from the rotor, the remaining components of the blood primarily red blood cells-are urged from the rotor and directed through valve 27 and filter 17, and into the RBC-storage container 28. Filter 17 removes white blood cells from the red blood cells and allows the red blood cells to pass through to the RBC-storage container 28. The RBC-storage container 28 is preferably a bag and preferably contains RBC-storage solution. The RBC-storage bag 28 preferably holds a unit of red blood cells. Valve 27 is controlled by the control unit 20.

In order to reduce the amount of red blood cells left in the WBC filter 17 after the rotor 21 has been emptied, several strategies may be used: After the plasma component has been urged from the rotor 21 into plasma-storage container 24, the RBC-storage solution may be urged from the RBC-storage container 28 into the rotor 21 to mix with the red blood cell component left in the rotor 21. (The movement of the RBC-storage solution may be accomplished by a vacuum in the chuck holding the rotor 21 and/or by another pumping mechanism working on the tubing between the RBC-storage container 28 and the rotor 21, for example.) By diluting the red blood cells with storage solution before the red blood cells are sent through the filter 17, the volume of liquid caught in the filter (and in the tubing leading from the rotor) will contain fewer red blood cells than if undiluted red blood cells were sent through the filter 17.

Figure 4:
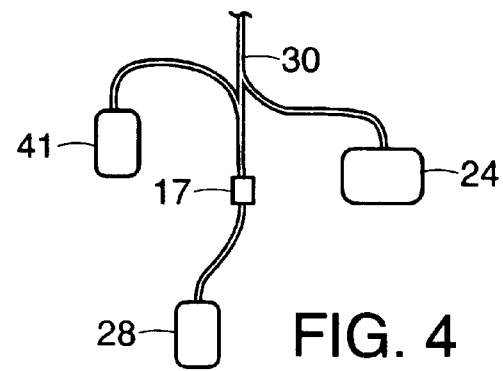
FIG. 4 shows a variation on the disposable set of FIG. 3.

In another strategy, an additional bag is added to the disposable set shown in FIG. 3. This additional bag is connected to an additional branch of tubing between the filter 17 and the rotor 21. This additional bag contains RBC-storage solution. Such a variation on the disposable set is shown in FIG. 4, which shows only a portion of this alternative disposable set; FIG. 4 does not show the rotor, the anticoagulant/plasma bag and the needle. FIG. 4 shows an RBC-preservative container 41 attached to a branch of the tubing 30 between the rotor and the filter 17. The FIG. 4 disposable set is initially provided with the RBC preservative (or storage solution) in RBC-preservative container 41 instead of in the RBC-storage container 28. After the red blood cells pass through the WBC filter 17 and into RBC-storage container 28, RBC-preservative may be urged (by a pumping mechanism working on the tubing, for instance) from container 41 through the filter 17 into the RBC-storage container 28. Passing preservative solution through the filter 17 rinses additional red blood cells out of the filter into the storage containers 28, and thus almost all the red blood cells are urged from the filter into the RBC-storage container 28. Some of the RBC preservative may be mixed with the red blood cells before they pass through the filter.

After the storage container 28 is filled with red blood cells, the RBC-storage container 28 may be removed from the rest of the disposable set by cutting and heat sealing the tubes leading to the containers.

The disposable sets the cannula 10, the plasma storage bag 24, the RBC storage bag 28, WBC filter 17, centrifuge rotor 21 and the tubing—may be configured in several ways. For instance, the tubing may consist solely of tubes which may be squeezed by the control unit to direct flow or to pump in a peristaltic manner. Alternatively, the tubing may contain special valving or pumping components (such as a pumping/valving cassette) which may be acted on by the control unit. The phrase "flow-control arrangement" refers herein to any structure or system for controlling or causing flow of fluid between the various components of the systems of the present invention.

Depending on the maximum volume of the centrifuge rotor 21 used, it may be necessary to go through several cycles of filling the rotor, separating the blood into red blood cell and plasma components and urging blood components from the rotor. Preferably, however, a large enough rotor is used so that the donor may be disconnected from the system before the blood is processed. Once the storage bags 24, 28 are filled with their respective components, the storage bags are removed from the rest of the disposable set by cutting and heat sealing the tubes leading to the storage bags.

The process described herein above is highly automated compared to the prior-art methods of processing blood. A blood-donation technician installs the disposable set into the control unit 20 and inserts the cannula 10 into the donor's arm. The technician, of course, also removes the needle from the donor's arm, and cuts and heat seals the tubing leading to the storage bags. (The control unit may be provided with an interlock device to ensure that the needle is removed from the donor's arm before the control unit begins pumping any blood components out of the rotor.) The remaining steps of the process may be performed by the control unit: controlling the valves (and any pumps) to direct the flow of blood or blood components; determining when the rotor is sufficiently full; spinning the rotor; urging blood components from the rotor; and determining when the rotor has been emptied of a blood component.

Figure 5:
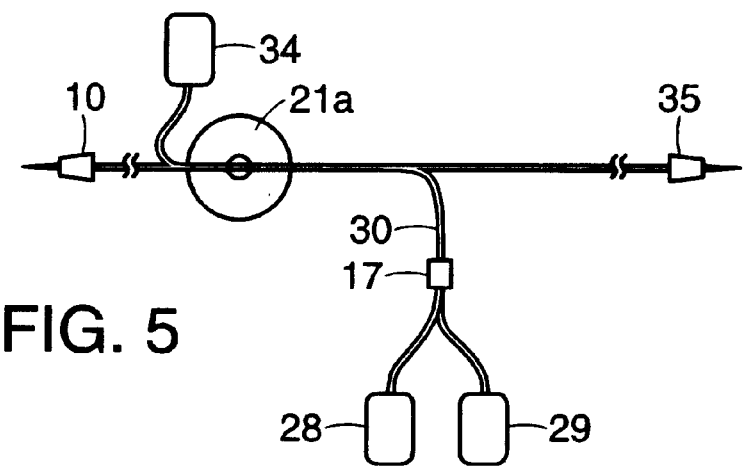
FIG. 5 shows a disposable set for use in an alternative system, which collects whole blood from a donor and returns less than all of the collected blood components to the donor.
Figure 11:
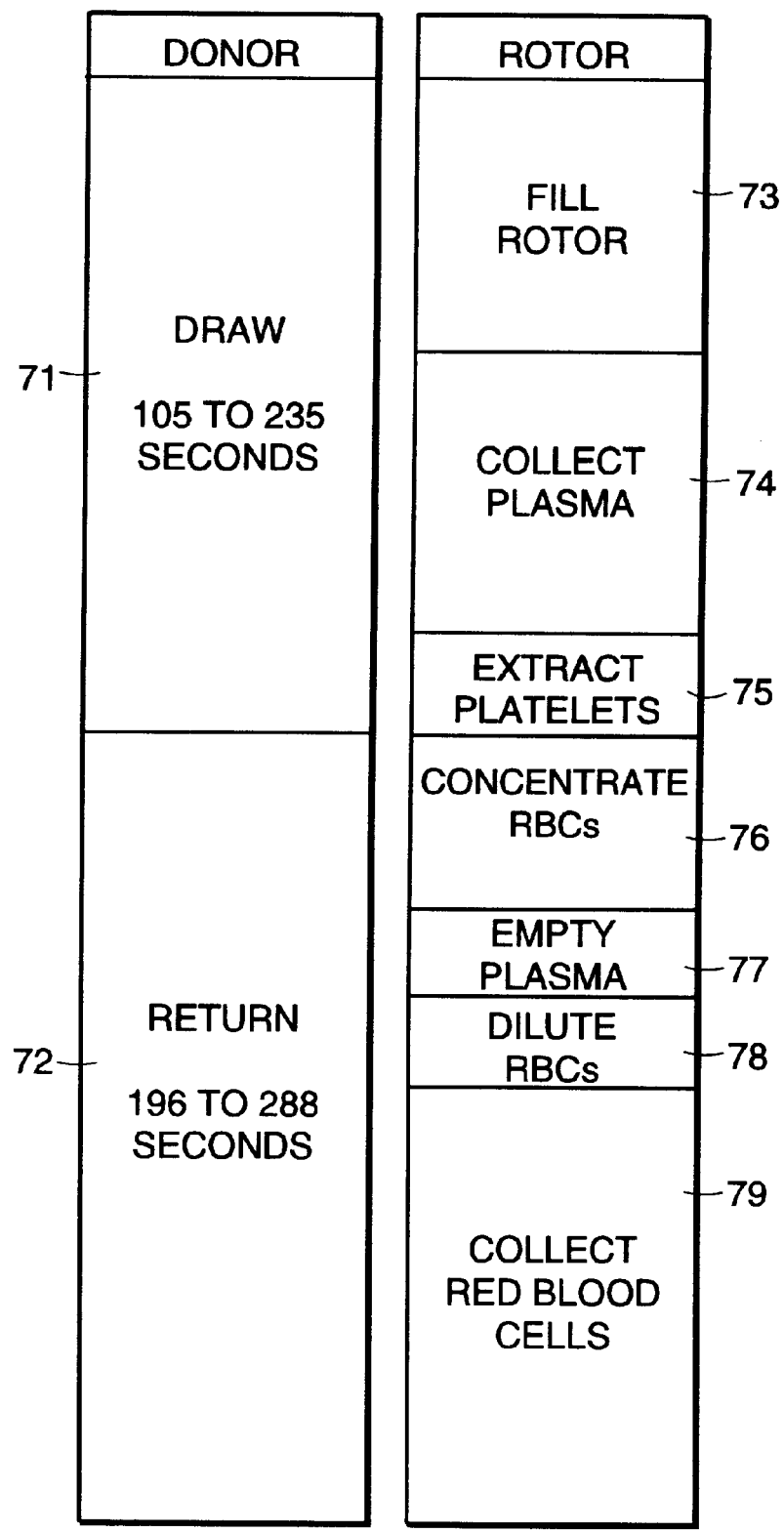
FIG. 11 shows the arrangement of steps in a cycle of a process for collecting red blood cells using the disposable set of FIG. 10.

In an alternative embodiment, such as the embodiment shown in FIG. 5, the disposable set may include a rotor 21a having two conduits (such as the rotors shown in FIGS. 11 and 23 of above-referenced U.S. Pat. No. 5,733,253) so as to permit the removal of a separated blood component (preferably plasma) from the rotor at the same time as whole blood is being introduced into the rotor. the plasma may be collected in a storage container, or as shown in the FIG. 5 embodiment, a second cannula 35 may be connected to the outlet portion of the tubing from the rotor 21a, so that plasma may be returned to the donor while whole blood is being removed from the donor.

Like the FIG. 3 set, the FIG. 5 set includes a cannula 10 or other device for permitting whole blood to enter the disposable set. The whole blood passes from the cannula 10 through tubing into the rotor 21a, and a valve or a pump or other flow-control arrangement controls the flow of whole blood into the disposable set. Anticoagulant may be introduced from anticoagulant container 34 to the whole blood entering the rotor 21a. A metering valve on the control unit may be used to meter the anticoagulant from the anticoagulant container 34 into the whole blood being drawn from the cannula 10. In a preferred embodiment, the tubing may be modified so that the anticoagulant is added to the whole blood coming from the donor at a point in the tubing much closer to the cannula 10.

The tubing has a portion that provides whole blood to the inlet of the rotor 21a and another portion that provides blood components from the rotor's outlet to outlet cannula 35 and to the RBC-collection containers 28, 29; the outlet portion of the tubing also includes a WBC filter 17 between the rotor 21a and the RBC-collection containers 28, 29.

When a sufficient amount of whole blood has entered the rotor 21a, the rotor is spun sufficiently fast so as to separate the blood into plasma and RBC components. After the blood has separated into plasma and red blood cells, plasma is urged from the rotor 21a and is directed back to the donor through the return cannula 35—or, in an alternative embodiment, as noted above, a plasma-storage container may be substituted for the return cannula 35, and the plasma may be directed to the plasma-storage container instead of being returned to the donor. Whole blood may continue to enter the rotor 21a, as plasma is being removed from the rotor.

When the rotor 21a is filled with red blood cells, or when it is otherwise determined that enough red blood cells have been collected, whatever remains of the plasma is urged from the rotor 21a, and by means of a flow-control arrangement on the control unit, red blood cells are urged from the rotor 21a through the WBC filter 17, which filters white blood cells from the red blood cells, to RBC-storage container 28. Depending on the maximum volume of the centrifuge rotor 21a used, it may be necessary to go through several cycles of filling the rotor, separating the blood into red blood cell and plasma components and urging blood components from the rotor, in order to fill RBC container 28.

If the plasma component of the blood is being returned to the donor, two units of red blood cells may ordinarily be collected from the donor. In accordance with industry practice, the two units of red blood cells may be stored in two separate containers 28 and 29. After the first RBC-storage container 28 is filled with a unit of blood, additional red blood cells may be urged from the rotor 21a and then are directed, by means of a flow-control arrangement on the control unit, into the second RBC-storage container 29. As noted above, depending on the maximum volume of the centrifuge rotor 21a in relation to the total volume of the two RBC-storage containers 28, 29 used, it may be necessary to go through several cycles of filling the rotor, separating the blood into red blood cell and plasma components and urging blood components from the rotor, in order to fill both RBC-storage containers 28 and 29. The storage containers 28 and 29 are preferably bags and preferably contain RBC-storage solution. Each of the RBC-storage bags 28 and 29 preferably holds a unit of RBCs.

Once the storage bags 28, 29 are filled with their respective components, the storage bags are removed from the rest of the disposable set by cutting and heat sealing the tubes leading to the storage bags.

Like the disposable set of FIG. 3, the disposable set shown in FIG. 5—the inlet cannula 10, the outlet cannula 35, the storage bags 28, 29, WBC filter 17, centrifuge rotor 21 and the tubing may be configured in several ways. For example, in lieu of simple tubing, which may be squeezed, alternative flow-control arrangements may be used, such as a pumping/valving cassette acted on by the control unit. Two other examples of the variations are shown in FIGS. 6 and 7.

Figure 6:
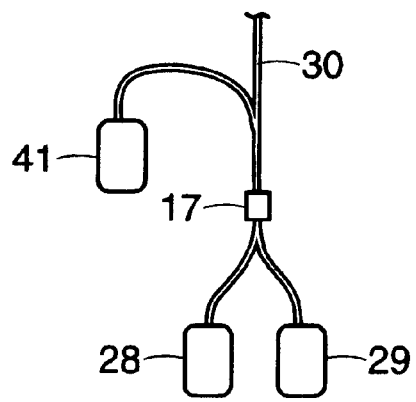
FIGS. 6 and 7 show variations on the disposable set of FIG. 5.
Figure 7:
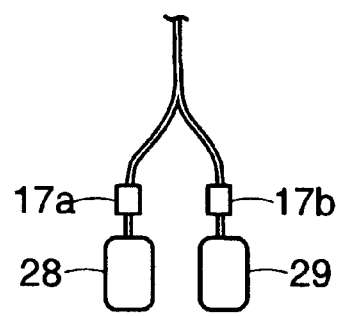

The disposable-set configurations shown in FIGS. 6 and 7 have two RBC-storage containers 28, 29, each of which preferably hold one unit of re cells in accordance with industry practices. Alternative embodiments of the disposable sets may include only one RBC-storage container (and/or may use an RBC-storage container that holds an amount different from one unit). FIGS. 6 and 7 show only a portion of alternative disposable sets; they do not show the rotor, the anticoagulant bag and the needles. FIG. 6 shows an RBC-preservative container 41 attached to a branch of the tubing 30 between the rotor and the filter 17. The FIG. 6 disposable set is initially provided with the RBC preservative (or storage solution) in RBC-preservative container 41 instead of in the RBC-storage containers 28, 29. After the red blood cells pass through filter 17, which filters out the white blood cells, and into RBC-storage containers 28, 29, RBC-preservative may be urged from container 41 through the WBC filter 17 into the RBC-storage containers 28, 29. As with the disposable set embodiment shown in FIG. 4, passing preservative solution through the filter 17 rinses additional red blood cells out of the filter into the storage containers 28, 29. Some of the RBC preservative may be mixed with the red blood cells before they pass through the filter. After the storage containers 28, 29 are filled with red blood cells, the storage containers may be removed from the rest of the disposable set by cutting and heat sealing the tubes leading to the containers. FIG. 7 shows a portion of an embodiment that is similar to the embodiment shown in FIG. 5 but which includes two WBC filters 17a, 17b, one for each of the RBC-storage containers 28, 29.

Figure 8:
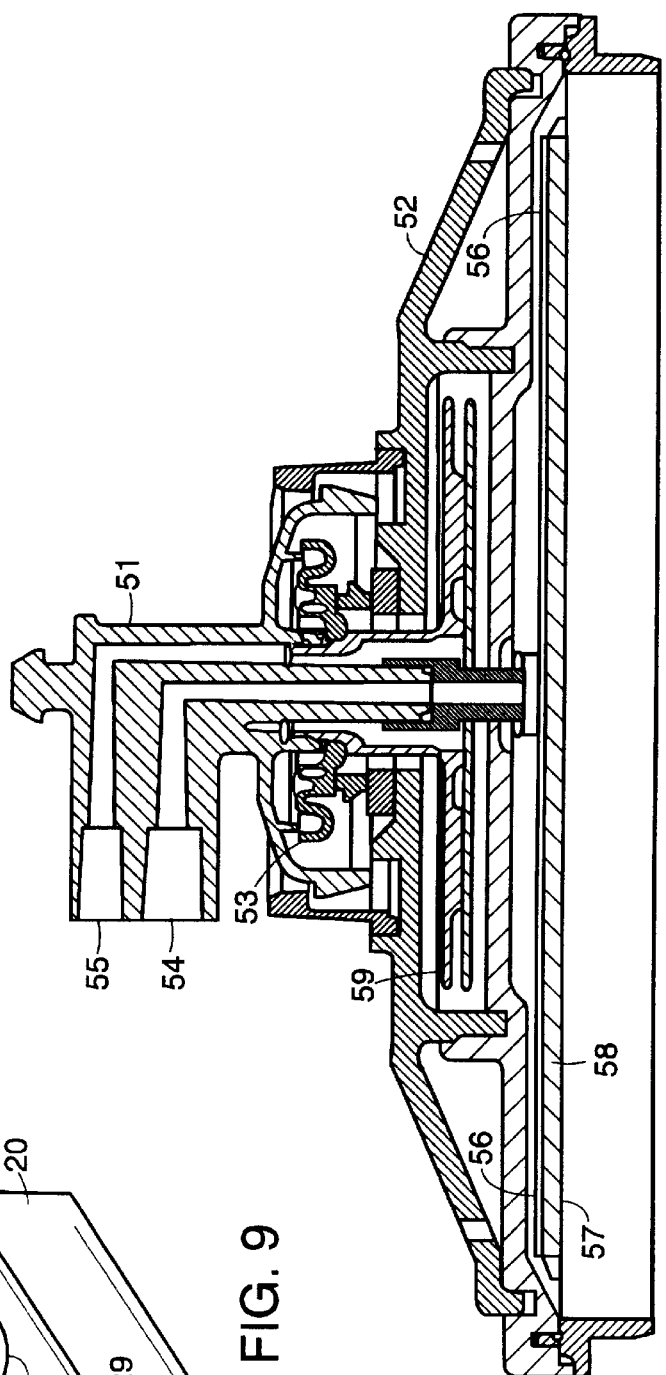
FIG. 8 shows a sectional view of a rotor that may be used in the disposable set of FIG. 5.

FIG. 8 is a sectional view of a rotor which may be used in the disposable set shown in FIG. 5, and which is a variation on the rotor shown in FIGS. 10–15 of U.S. Pat. No. 5,733,253. The rotor includes a fixed portion 51, which does not rotate and which is held in place by a brace on a control unit that is adapted to control the disposable set of FIG. 5; a rotatable portion 52, which is held and spun by a chuck in the control unit; and a rotary seal 53, which maintains a seal between the fixed portion and the rotatable portion. The rotary seal preferably works in the same manner as the rotary seal shown in FIGS. 38 and 39 of U.S. Pat. No. 5,733,253: The sealing force applied by the rotary seal 53 is not substantially affected by changes in air pressure within the rotor. The rotary seal is mounted on a base, which may be part of the rotor's fixed portion 51. The rotary seal 53 includes first and second rigid seal members, which surround the axis of rotation, and which spin in relation to each other. As set forth in patent Ser. No. 5,733,253, the first rigid seal member and the base define an annular passage between them, and the first rigid seal member has a step portion which extends radially across the annular passage. A spring member surrounds the rotary seal's axis of rotation and is connected to the base and to the first rigid seal member, so that the spring member applies a force pressing the first rigid seal member against the second rigid seal member. A flexible seal member surrounds the axis of rotation and prevents fluid flow between the first rigid seal member and the base. The flexible seal member extends across the annular passage such that pressure from the annular passage exerts forces on the flexible seal member and the step portion which cancel each other, so that the force with which the spring member presses the first rigid seal member against the second rigid seal member is not substantially affected by pressure within the annular passage.

The rotor's fixed portion includes a rotor inlet 54 and a rotor outlet 55, which are connected by tubing with the rest of the disposable set. The tubing of the disposable set has a portion that provides whole blood to the inlet of the rotor 21 and another portion that provides blood components from the rotor's outlet to cannula 35 and to the RBC-collection containers 28, 29. The inlet rotor port 54 leads to a fluid passage down the fixed portion to a pair of channels 56, which are in the rotor's rotatable portion 52. The channels 56 permit the whole blood that has come from the donor to flow to the outer perimeter of the rotor's interior volume. Because the rotor's interior volume is defined in part by a flexible, preferably elastic, diaphragm, the rotor has a variable total volume.

Preferably, only two such inflow channels 56 providing fluid communication from the inlet rotor port 53 are used, in order to minimize the amount of blood trapped in the rotor when the process is completed, and these two channels are preferably disposed 180° to each other, in order to maintain balance in the rotor. In alternative embodiments, one or more than two inflow channels 56 may be used. The rotor includes an interior wall 58, which together with the flexible diaphragm 57 fully define the rotor's processing chamber. The interior wall 58 includes grooves on its bottom surface (not shown), which permit flow of blood components out of the rotor's processing chamber. In a preferred embodiment, the interior wall 58 includes two of these outflow grooves arranged 180° C. to each other and at 90° C. to the inflow channels 56. The outflow grooves lead to holes which pass up through the interior wall 58 to the region adjacent a collector 59. These holes (not shown) provide fluid communication between the outflow grooves and the collector 59, which is part of the rotor's fixed portion 51. The collector 59 collects the blood components flowing out of the processing chamber and directs the blood components up through a vertical passage to the outlet rotor port 55.

Figure 9:
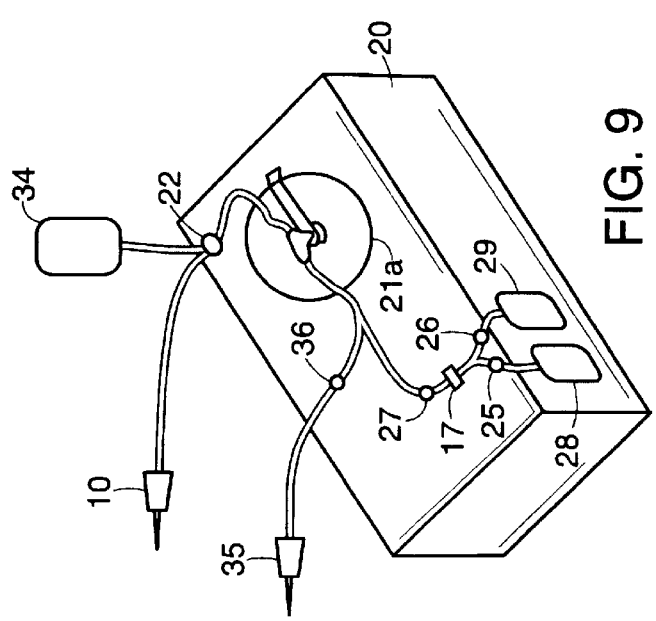
FIG. 9 shows a system that uses the disposable set of FIG. 5.

FIG. 9 shows a control unit 20 adapted to receive and control the disposable set of FIG. 5. The control unit 20 preferably includes a chuck for holding and spinning the rotor 21a, a pump for changing the pressure against the rotor's elastic diaphragm, a flow-control arrangement for controlling flow through the disposable set, and an electronic controller for controlling the chuck, the pump and the flow-control arrangement. The flow-control arrangement includes a valve 22 for controlling the flow of whole blood into the rotor and for metering the correct amount of anticoagulant into the whole blood, a valve 36 for controlling the flow of plasma back to the outlet cannula 35 and the donor, and a set of valves 27, 25, 26 for controlling flow to the WBC filter and the RBC storage bags 28, 29.

Figure 10:
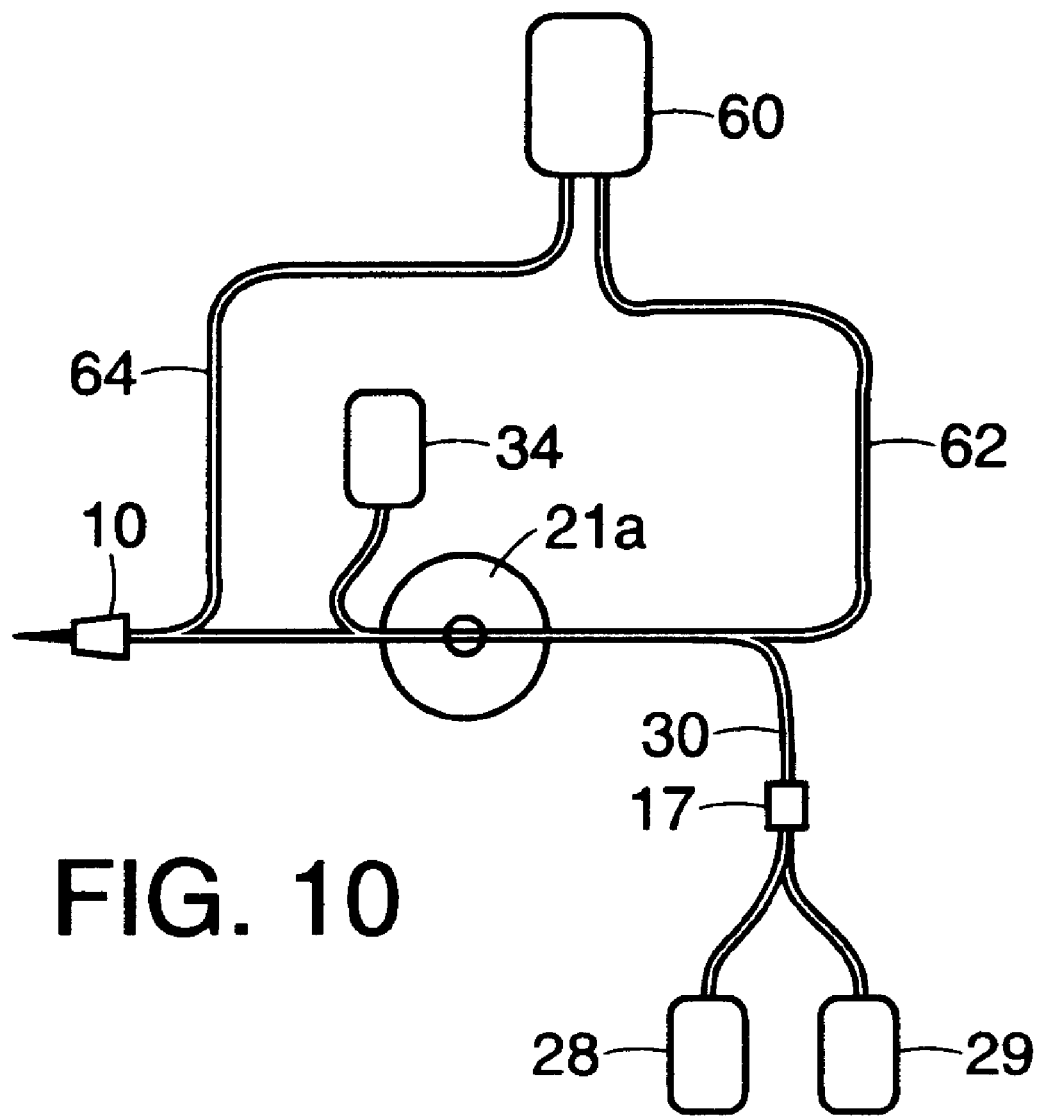
FIG. 10 shows an alternative disposable set.

The disposable set and the control unit 20 shown in FIG. 9 may in a preferred embodiment be modified to use a single cannula to draw whole blood from the donor and return plasma to the donor. Such a disposable set is shown in FIG. 10. A temporary storage container 60 holds the separated plasma component for return to the donor. The separated plasma component is urged by the control unit from the rotor 21a through a portion 62 of the tubing to the temporary storage container 60. The control unit preferably urges the plasma from the rotor by increasing the gas pressure against the rotor's elastic membrane. Once plasma begins flowing from the rotor, the continued introduction of whole blood to the rotor tends to continue forcing separated plasma out of the rotor. After a desired amount of whole blood has been collected from the donor through cannula 10 (preferably when the rotor is almost full of red blood cells), the collection of whole blood is suspended, and plasma may be urged from the temporary storage container 60 through another portion 64 of the tubing to the cannula 10 and the donor. The control unit may be provided with means, such as a peristaltic pump working on tubing portion 64, for effecting and controlling the flow of plasma from the temporary storage container 60 to the cannula 10. The rest of the disposable set may be same as the disposable set shown in FIG. 5, including a WBC filter 17 in another portion 30 of the tubing leading from the rotor 21a to the RBC storage containers 28 and 29. An anticoagulant container 34 may be attached to the portion of the tubing leading from the cannula 10 to the rotor 21a. In a preferred embodiment, the anticoagulant container may be connected to a point in the tubing closer to the cannula 10, so as to introduce the anticoagulant to the whole blood as soon as possible after it is drawn from the donor.

The process of collecting red blood cells using the disposable set shown in FIG. 10 may involve several cycles of collecting whole blood from the donor and returning the separated plasma component to the donor. FIG. 11 shows an outline of steps in one such cycle. Each cycle is divided up into two periods: a first period 71 in which whole blood is drawn from the donor, i.e., a draw period (which in one embodiment lasts between 105 and 235 seconds), and a second period 72 in which plasma is returned to the donor, i.e., a return period (which lasts between 196 and 288 seconds). During the draw period 71, the rotor—item 21a in FIG. 10—is filled with whole blood from the donor (step 73), and the rotor is spun to separate the blood into plasma and RBC components. Plasma is urged from the rotor to the temporary container 60 (step 74—of course, some of these steps may overlap).

In an optional step (step 75), the platelets may be separately collected in the manner set forth in concurrently filed application Ser. No. 09/271,601, for a "System and Method for Collecting Platelets and Other Blood Components," and listing Thomas D. Headley as an inventor. (As set forth previously, this concurrently filed application is incorporated herein by reference.) During the return period 72, the red blood cells are concentrated, by increasing the rotational speed of the centrifuging rotor (step 76), and the remaining plasma is removed from the rotor 21a to the temporary container 60 (step 77). An RBC-storage solution may be added to the red blood cells, diluting the red blood cells (step 78). In the final step of the cycle (step 79), the red blood cells are directed through the portion 30 of the tubing containing the filter 17, which removes the white blood cells from the red blood cells. After passing through the WBC filter, the red blood cells are directed to one of the two storage containers 28 or 29.

When the red blood cells have been moved from the rotor to the storage containers, and when the plasma in the temporary container has been returned to the donor, the cycle may start again with the draw period 71 and the rotor filling step 73. In one embodiment, the total cycle time lasts from 5 to 8.7 minutes (assuming a hematocrit range of 40 to 55 and a draw speed range of 60 to 100 ml/min). Four cycles may be executed, for a total procedure time of 20 to 34.8 minutes.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A method of processing blood, the method comprising:
   providing a disposable set having an access means for withdrawing blood, an RBC container, a centrifuge rotor having a variable total volume, a filter and tubing connecting the access means, the container, the rotor and the filter;
   providing a control unit having a spinner means for loading and spinning the rotor;
   placing the rotor in the spinner means;
   drawing whole blood through the access means;
   directing the whole blood from the access means through the tubing to the rotor;
   causing the spinner means to rotate the rotor so as to separate the whole blood into a first component and a second component, wherein the first component is primarily plasma, and wherein the second component is primarily red blood cells and includes white blood cells;
   urging the first and second components out of the rotor, wherein at least one of the first and second components is urged out of the rotor while the rotor is still spinning;
   directing the second component through the filter so that white blood cells are caught in the filter and red blood cells pass through the filter; and
   directing the red blood cells from the filter to the RBC container.

2. The method according to claim 1, wherein the disposable set includes return means, and wherein the method further includes the steps of drawing whole blood from a donor through the access means and directing the first component back to the donor through the return means.

3. A method of processing blood, the method comprising:
   providing a disposable set having an access means for withdrawing blood, an RBC container for containing one unit of red blood cells, a plasma container for containing one unit of plasma, a centrifuge rotor having a variable total volume, a filter and tubing connecting the access means, the RBC container, the plasma container, the rotor and the filter;
   providing a control unit having a spinner means for loading and spinning the rotor;
   placing the rotor in the spinner means;
   connecting the access means to a donor;
   drawing one unit of whole blood through the access means, while the rotor is in the spinner means;
   directing the whole blood from the access means through the tubing to the rotor;
   disconnecting the donor from the access means after one unit of whole blood has been collected;
   causing the spinner means to rotate the rotor so as to separate the whole blood into a first component and a second component, wherein the first component is primarily plasma, and wherein the second component is primarily red blood cells and includes white blood cells;
   urging the first and second components out of the rotor, wherein at least one of the first and second components is urged out of the rotor while the rotor is still spinning;
   directing the first component from the rotor to the plasma container;
   directing the second component directly from the rotor to and through the filter so that white blood cells are caught in the filter and red blood cells pass through the filter; and
   directing the red blood cells from the filter to the RBC container.

4. The method according to claim 3, wherein the centrifuge rotor has a variable total volume.

5. The method according to claim 4, wherein the centrifuge rotor is provided with a fixed portion, a rotatable portion and a rotary seal providing a seal between the fixed and rotatable portions, and the tubing is connected to the rotor's fixed portion.

6. The method according to claim 5, wherein the control unit varies the volume of the centrifuge rotor.

7. The method according to claim 6, wherein the centrifuge rotor is provided with a flexible diaphragm which defines the volume of the rotor, and the control unit is provided with means for varying air pressure adjacent the flexible diaphragm so as to vary the total volume of the centrifuge rotor.

8. The method according to claim 3, wherein the donor is disconnected from the access means prior to urging the second component from the rotor.

9. The method according to claim 8, wherein the donor is disconnected from the access means prior to urging the first component from the rotor.

10. The method according to claim 9, wherein the donor is disconnected from the access means prior to the spinner means rotating the rotor to separate the whole blood into first and second components.

11. The method according to claim 3, wherein the centrifuge rotor is provided with a fixed portion, a rotatable portion and a rotary seal providing a seal between the fixed and rotatable portions, and the tubing is connected to the rotor's fixed portion.

12. A method of processing blood, the method comprising:
providing a disposable set having an access means for withdrawing blood, an RBC container, a plasma container, a centrifuge rotor having a variable total volume, a filter and tubing connecting the access means, the RBC container, the plasma container, the rotor and the filter;
providing a control unit having a spinner means for loading and spinning the rotor;
placing the rotor in the spinner means;
connecting the access means to a donor;
drawing whole blood through the access means;
directing the whole blood from the access means through the tubing to the rotor;
causing the spinner means to rotate the rotor so as to separate the whole blood into a first component and a second component, wherein the first component is primarily plasma, and wherein the second component is primarily red blood cells and includes white blood cells;
urging the first and second components out of the rotor, wherein at least one of the first and second components is urged out of the rotor while the rotor is still spinning;
directing the first component from the rotor to the plasma container;
directing the second component directly from the rotor to and through the filter so that white blood cells are caught in the filter and red blood cells pass through the filter; and
directing the red blood cells from the filter to the RBC container.

13. The method according to claim 12, wherein whole blood is drawn through the access means and directed to the rotor while the rotor is mounted in the spinner means.

14. The method according to claim 13, wherein the donor is disconnected from the access means prior to urging the second component from the rotor.

15. The method according to claim 14, wherein the donor is disconnected from the access means prior to urging the first component from the rotor.

16. The method according to claim 15, wherein the centrifuge rotor has a variable total volume.

17. The method according to claim 16, wherein the centrifuge rotor is provided with a fixed portion, a rotatable portion and a rotary seal providing a seal between the fixed and rotatable portions, and the tubing is connected to the rotor's fixed portion.

18. The method according to claim 17, wherein the control unit varies the volume of the centrifuge rotor.

19. The method according to claim 18, wherein the centrifuge rotor is provided with a flexible diaphragm which defines the volume of the rotor, and the control unit is provided with means for varying air pressure adjacent the flexible diaphragm so as to vary the total volume of the centrifuge rotor.

20. The method according to claim 15, wherein the donor is disconnected from the access means prior to the spinner means rotating the rotor to separate the whole blood into first and second components.

21. The method according to claim 12, wherein the centrifuge rotor is provided with a fixed portion, a rotatable portion and a rotary seal providing a seal between the fixed and rotatable portions, and the tubing is connected to the rotor's fixed portion.

22. The method according to claim 21, wherein the centrifuge rotor has a variable total volume.

23. A system for processing blood, the system comprising:
a disposable set having
a container;
a centrifuge rotor having a variable total volume;
a filter that filters white blood cells from red blood cells passing through the filter, the filter being located in a fluid path between the centrifuge rotor's fixed portion and the container; and
an access means for withdrawing blood, in fluid communication with the centrifuge rotor, for permitting the introduction of blood into the rotor;
a control unit having
a spinner means for loading and spinning the rotor so as to separate blood into blood components; and
a flow-control arrangement which urges a blood component from the rotor while the rotor is being spun.

24. The system according to claim 23, wherein the control unit further includes means for varying the volume of the rotor.

25. A disposable set for processing blood, the disposable set comprising:
a container;
a centrifuge rotor having a variable total volume and having a fixed portion, a rotatable portion and a rotary seal providing a seal between the fixed and rotatable portions;
a filter that filters white blood cells from red blood cells passing through the filter;
tubing that connects the container, the rotor's fixed portion and the filter, wherein the filter is located in the tubing between the container and the centrifuge rotor; and
an access means for withdrawing blood, in fluid communication with the tubing, for permitting the introduction of blood into the tubing;
wherein the rotary seal includes:
a base;
first and second rigid seal members, which surround the axis of rotation and which spin in relation to each other, the first rigid seal member and the base defining an annular passage between them, the first rigid seal member having a step portion which extends radially across the annular passage;

a spring member surrounding the rotary seal's axis of rotation and connected to the base and to the first rigid seal member so that the spring member applies a force pressing the first rigid seal member against the second rigid seal member; and a flexible seal member surrounding the axis of rotation and preventing fluid flow between the first rigid seal member and the base, the flexible seal member extending across the annular passage such that pressure from the annular passage exerts forces on the flexible seal member and the step portion which cancel each other, so that the force with which the spring member presses the first rigid seal member against the second rigid seal member is not substantially affected by pressure within the annular passage.

26. A disposable set for processing blood, the disposable set comprising:

container;

a centrifuge rotor having a fixed portion, a rotatable portion and a rotary seal providing a seal between the fixed and rotatable portions, wherein the centrifuge rotor has a variable total volume;

a filter that filters white blood cells from red blood cells passing through the filter;

tubing that connects the container, the rotor's fixed portion and the filter; and an access means for withdrawing blood, in fluid communication with the tubing, for permitting the introduction of blood into the tubing;

wherein the rotary seal includes:

a base;

first and second rigid seal members, which surround the axis of rotation and which spin in relation to each other, the first rigid seal member and the base defining an annular passage between them, the first rigid seal member having a step portion which extends radially across the annular passage;

a spring member surrounding the rotary seal's axis of rotation and connected to the base and to the first rigid seal member so that the spring member applies a force pressing the first rigid seal member against the second rigid seal member; and a flexible seal member surrounding the axis of rotation and preventing fluid flow between the first rigid seal member and the base, the flexible seal member extending across the annular passage such that pressure from the annular passage exerts forces on the flexible seal member and the step portion which cancel each other, so that the force with which the spring member presses the first rigid seal member against the second rigid seal member is not substantially affected by pressure within the annular passage.

27. A system for processing blood, the system comprising:

a disposable set having a container;

a centrifuge rotor having a variable total volume and including an elastic diaphragm that defines the volume of the rotor;

a filter that filters white blood cells from red blood cells passing through the filter, the filter being located in a fluid path between a fixed portion of the centrifuge rotor and the container; and an access means for withdrawing blood, in fluid communication with the centrifuge rotor, for permitting the introduction of blood into the rotor; and a control unit having a spinner means for loading and spinning the rotor so as to separate blood into blood components; and a flow-control arrangement which urges a blood component from the rotor while the rotor is being spun.

28. A system according to claim 27, wherein the control unit includes means for varying gas pressure adjacent the elastic diaphragm.

* * * * *